US007326719B2

(12) United States Patent
Hickey et al.

(10) Patent No.: US 7,326,719 B2
(45) Date of Patent: Feb. 5, 2008

(54) CATHEPSIN S INHIBITORS

(75) Inventors: Eugene R. Hickey, Danbury, CT (US); Weimin Liu, Sandy Hook, CT (US); Sanxing Sun, Danbury, CT (US); Yancey David Ward, Sandy Hook, CT (US); Erick Richard Roush Young, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 708 days.

(21) Appl. No.: 10/790,549

(22) Filed: Mar. 1, 2004

(65) Prior Publication Data

US 2004/0180886 A1 Sep. 16, 2004

Related U.S. Application Data

(60) Provisional application No. 60/454,239, filed on Mar. 13, 2003.

(51) Int. Cl.
*A61K 31/4468* (2006.01)
*A61K 31/453* (2006.01)
*C07D 413/12* (2006.01)

(52) U.S. Cl. ....................................... 514/317; 546/208

(58) Field of Classification Search ................ 546/208; 514/317
See application file for complete search history.

(56) References Cited

U.S. PATENT DOCUMENTS

| | | | | |
|---|---|---|---|---|
| 5,776,718 A | 7/1998 | Palmer et al. | | |
| 6,353,017 B1 | 3/2002 | Altmann et al. | | |
| 6,420,364 B1 * | 7/2002 | Emmanuel et al. | ...... | 514/231.5 |
| 6,492,362 B1 | 12/2002 | Graupe et al. | | |
| 6,506,733 B1 | 1/2003 | Buysse et al. | | |
| 6,525,052 B2 * | 2/2003 | Bekkali et al. | .......... | 514/237.2 |

FOREIGN PATENT DOCUMENTS

| | | |
|---|---|---|
| WO | WO 99/24460 | 5/1999 |
| WO | WO 00/49007 | 8/2000 |
| WO | WO 00/51998 | 9/2000 |
| WO | WO 01/19796 | 3/2001 |
| WO | WO 01/19808 | 3/2001 |

* cited by examiner

*Primary Examiner*—Kamal A. Saeed
*Assistant Examiner*—Janet L Coppins
(74) *Attorney, Agent, or Firm*—Michael Morris; Mary-Ellen M. Devlin; Anthony P. Bottino

(57) ABSTRACT

This invention relates to peptidyl compounds of the formulas (I) and (II) active as cathepsin S, a cysteine protease, inhibitors. The compounds are selective, reversible inhibitors of the cathepsin S are therefore useful in the treatment of autoimmune and other diseases. The invention also relates to processes for preparing such compounds and pharmaceutical compositions comprising them (I)

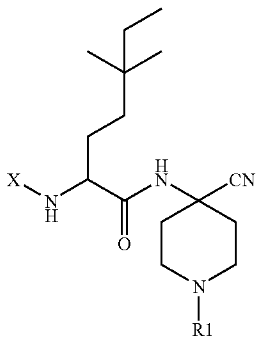

(II)

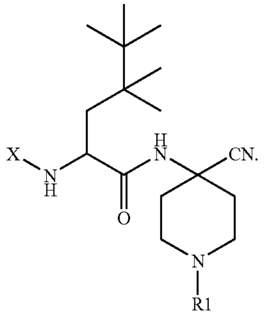

10 Claims, No Drawings

CATHEPSIN S INHIBITORS

APPLICATION DATA

This application claims benefit to U.S. provisional application No. 60/454,239 filed Mar. 13, 2003.

TECHNICAL FIELD OF THE INVENTION

This invention relates to peptidyl compounds active as cathepsin S, a cysteine protease, inhibitors. The compounds are selective, reversible inhibitors of the cathepsin S are therefore useful in the treatment of autoimmune and other diseases. The invention also relates to processes for preparing such compounds and pharmaceutical compositions comprising them

BACKGROUND OF THE INVENTION

Cathepsin S is a member of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207)

The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response.

Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dimers in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen-binding groove. CLIP is released from MHC Class II by the interaction of MHC Class II with HLA-DM, a MHC-like molecule thus freeing MHC Class II to associate with antigenic peptides. MHC Class II-antigen complexes are then transported to the cell surface for presentation to T-cells, and initiation of the immune response.

Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immunoregulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87), atherosclerosis (G. K. Sukhova et al., 1998, J. Clin. Invest., 102, 576) and endometriosis (WO 9963115, 1999).

A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation,1998, 101, 2351).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R. P. Hanzlik et al., 1991, Biochim. Biophys. Acta., 1073, 33), which are non-selective, inhibiting both cysteine and serine proteases as well as other nucleophiles. Peptidyl nitriles (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported. J. L. Klaus et al. (WO 96/40737) described reversible inhibitors of cysteine proteases including cathepsin S, containing an ethylene diamine. In U.S. Pat. No. 5,776,718 to Palmer et al. there is disclosed in it's broadest generic aspect a protease inhibitor comprising a targeting group linked through a two carbon atom chain to an electron withdrawing group (EWG). The compounds of the present application are structurally distinct and thus excluded from the U.S. Pat. No. 5,776,718 patent with particular embodiments possessing unexpectedly greater activity than the closest compounds of the prior art. U.S. Pat. No. 6,353,017 describes dipeptide nitriles asserted to have activity as inhibitors of Cathepsins B, K, L and S.

Examples of dipeptide nitrile-based cathepsin S inhibitors have been reported by Novartis application, WO 99/24460, 1999 and related U.S. Pat. No. 6,353,017. One of the generic structures is depicted below.

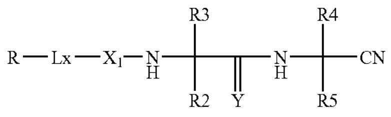

It is disclosed that R4 and R5 together represent lower alkylene, optionally interrupted by O, S, or NR6, so as to form a ring with the carbon atom to which they are attached, R3 is lower alkyl (defined as 1-7 carbon atoms branched or unbranched). However, in these documents, specific examples are limited to R4 and R5 being hydrogen, methyl, or joined together form cyclopropyl. No examples of R4 and R5 heterocyclic fusion are described. WO 99/24460 exemplifies larger R4 R5 fused carbocycles such as cyclohexyl but does not provide examples of heterocycles or teach that they will offer any advantage.

Furthermore although the description of R3 may generically encompass alkyl P2 side chains it does not exemplify specific structures providing the advantages of the present invention.

Another class of dipeptide nitrile-based cathepsin S inhibitors is described in U.S. Pat. No. 6,492,362. A specific example is claimed in this patent possessing an N-methyl piperidine P1 heterocycle. However, by definition the subject matter encompassed by U.S. Pat. No. 6,492,362 requires a sulfonyl containing P2 side chain as illustrated in the following generic structure.

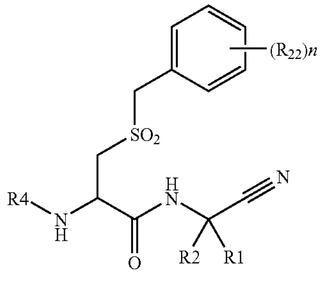

U.S. Pat. Nos. 6,525,052 and 6,420,364, commonly owned by the assignee of the present application, describe dipeptide nitrites bearing P1 heterocycles, the invention described herein provides a non-obvious benefit of improved selectivity profile.

Additional peptidyl nitrites have been reported as protease inhibitors. For example, both nitrites and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picomavirus protease. B. J. Gour-Salin (Can. J. Chem., 1991, 69, 1288) and T. C. Liang (Arch. Biochim. Biophys., 1987, 252, 626) described peptidyl nitrites as inhibitors of papain A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

A highly selective protease inhibitor also offers a more attractive therapeutic option. In general, selectivity is desired in order to avoid potential toxicities associated with inhibiting additional targets. Cathepsin L is a closely related family member of cathepsin S. Mice deficient of cathepsin L or possessing nonfunctional cathepsin L, have been shown to demonstrate numerous undesirable phenotypes including brain atrophy (U. Felbor et al., 2002, PNAS USA, 99 (12) 7883) progressive cardiomyopathy (J. Stypmann, et al., 2002, PNAS USA, 99 (9) 6234), impairment of the male reproductive system (W. W. Wright, et al., 2003, Biology of Reproduction, 68 (2) 680), and severe epidermal hyperplasia (F. Benavides, et al., 2002, American Journal of Patholog, 161 (2) 693).

In light of the above, there is a clear need for compounds which reversibly and selectively inhibit cathepsin S for indications in which these proteases exacerbate disease.

SUMMARY OF THE INVENTION

It is therefore an object of this invention to provide compounds as described herein which reversibly and selectively inhibit the cysteine protease cathepsin S. It is a further object of the invention to provide methods for treating diseases and pathological conditions exacerbated by these cathepsin S such as, but not limited, to rheumatoid arthritis, multiple sclerosis and asthma. It is yet a further object of the invention to provide processes for preparation of the above-mentioned compounds.

DETAILED DESCRIPTION OF THE INVENTION

The compounds of the invention feature specific P2 side chains 3,3-dimethyl pentyl(I), 2,2,3,3-tetramethyl butyl(II), and 3,3-dimethyl butyl(III) which substantially improve the selectivity profile of these inhibitors for cathepsin S over its closely related family member cathepsin L.

Accordingly, in one aspect of the invention, there are provided compounds of formulas (I), (II) and which are selective for cathepsin S:

(I)

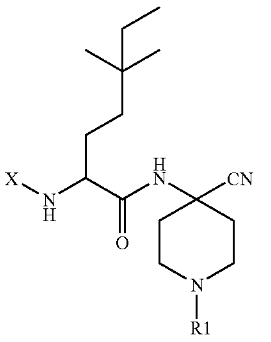

-continued (II)

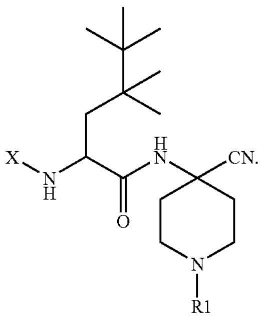

wherein X in each case is chosen from

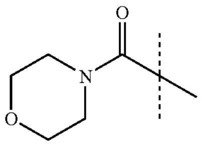

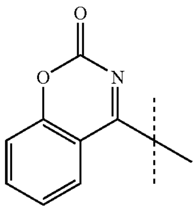

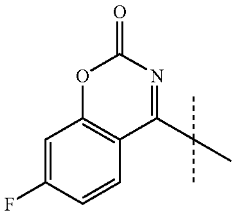

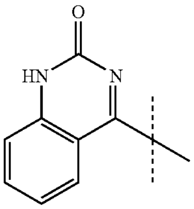

and

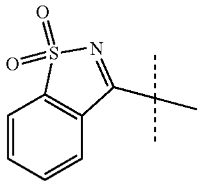

;

R1 is chosen from hydrogen or alkyl branched or straight chain alkyl, each carbon atom in the chain is optionally replaced with one to three heteroatoms chosen from O, S, and N—R2 wherein R2 is hydrogen or alkyl;

and wherein R1 is optionally further substituted by one or more alkoxy, amine, halogen, carbocycle, heteroaryl or heterocycle;

or the pharmaceutically acceptable salts thereof.

In another embodiment of the invention, there are provided compounds of the formula (I) as described immediately above (I)

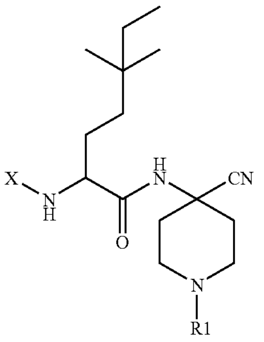

wherein X is chosen from

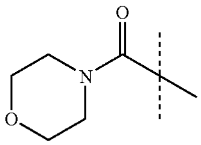

;

R1 is chosen from hydrogen or C1-10 alkyl branched or straight chain C1-10 alkyl, each carbon atom in the chain is optionally replaced with one to three heteroatoms chosen from O, S, and N—R2 wherein R2 is hydrogen or C1-5 alkyl;

and wherein R1 is optionally further substituted by one or more C-15 alkoxy, amine, heterocycle or halogen.

One preferred embodiment of R1 includes C1-5 alkyl, preferably C1-3 alkyl, most preferably methyl.

In another preferred embodiment of R1, R1 is chosen from:

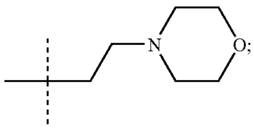

;

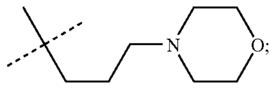

;

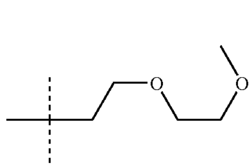

and

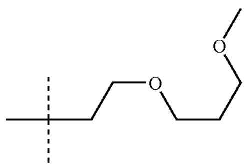

.

In a preferred embodiment of the invention, there are provided compounds of the formula (I) according to any of the embodiments described herein-above and wherein the indicated chiral carbon below is the (S) enantiomer which possesses a natural amino acid configuration (I)

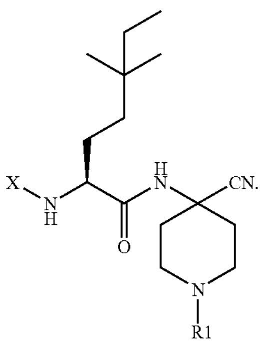

In another aspect of the invention, there is provided the following compounds which are selective for cathepsin S:

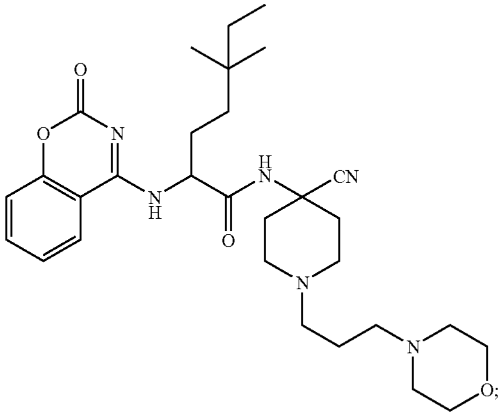

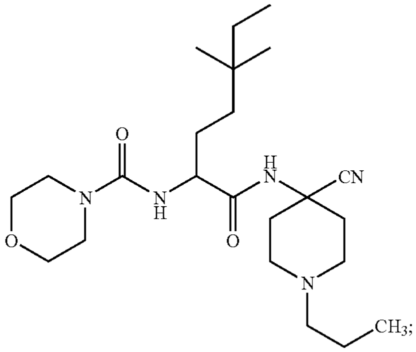

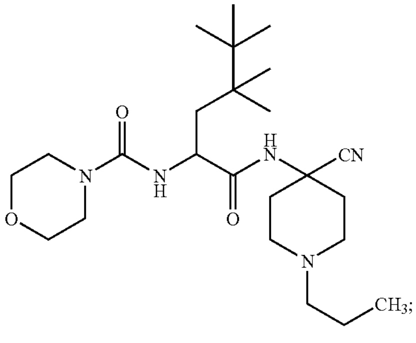

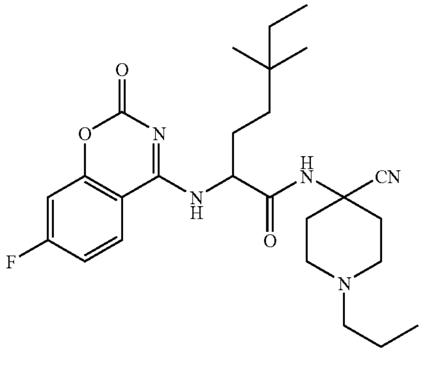

;

-continued

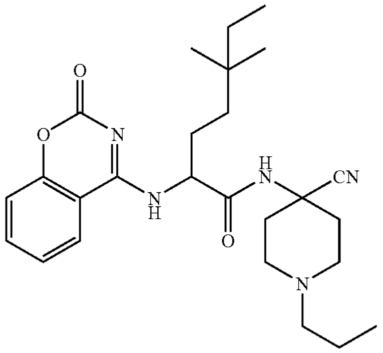

and

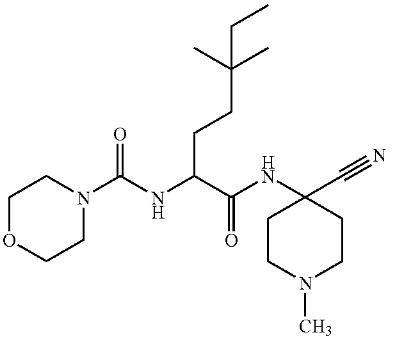

or the pharmaceutically acceptable salts thereof.

In another embodiment of the invention, there is provided the following compound which is selective for cathepsin S:

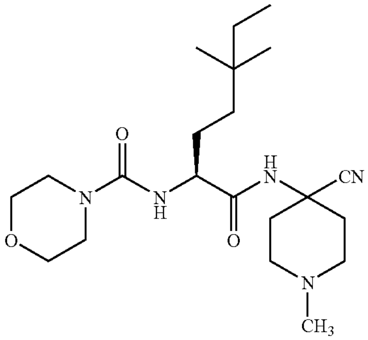

wherein the indicated chiral carbon below is the (S) enantiomer which possesses a natural amino acid configuration;

or the pharmaceutically acceptable salts thereof.

In a second aspect of the invention, there is provided the following compound of the formula (III) which is selective for cathepsin S:

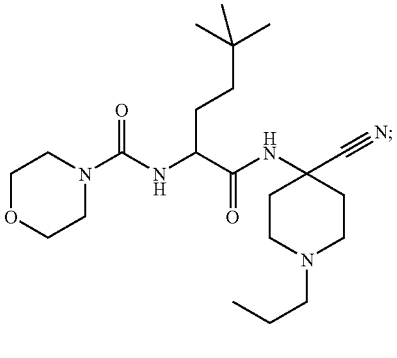

-continued

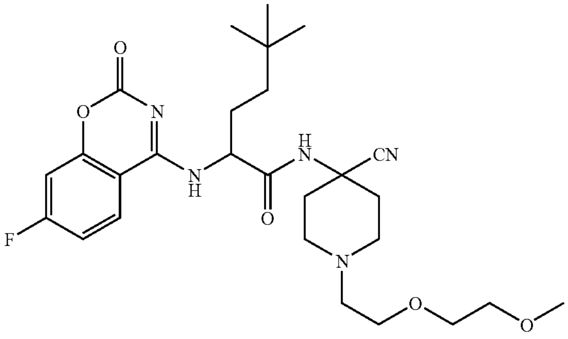

;

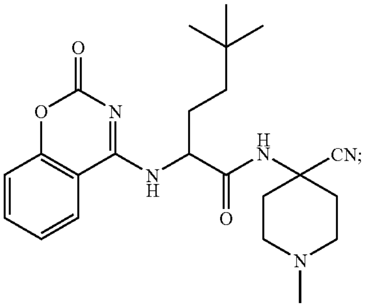

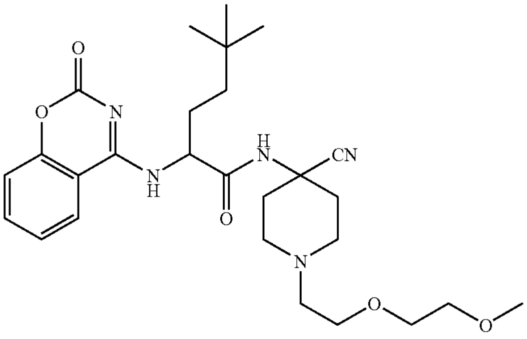

;

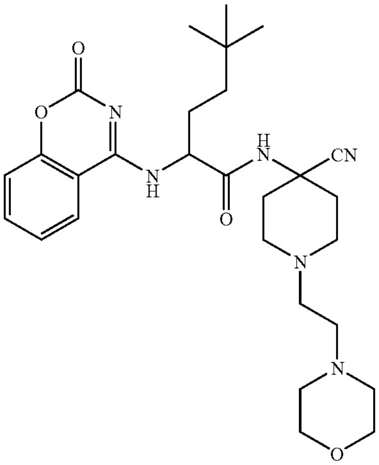

and

-continued

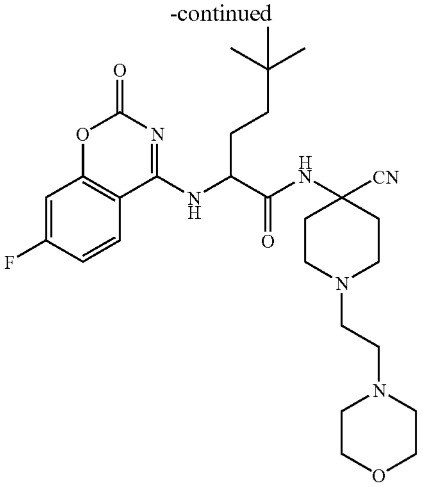

;

or the pharmaceutically acceptable salts thereof.

Unless otherwise noted, any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations.

In preferred compounds of the invention, the P2 chiral carbon is the (S) enantiomer which possesses a natural amino acid configuration.

Some of the compounds of the invention can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of the invention. A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

In addition, the compounds of this invention include prodrugs. Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of the invention, thereby imparting the desired pharmacological effect.

Of particular importance according to the invention are compounds of formulas (I), (II) or (III), wherein X and R1 have the meaning indicated, for use as pharmaceutical compositions with anti-cathepsin S activity.

The invention also relates to the use of a compound of formulas (I), (II) or (III), wherein X and R1 have the meaning indicated, for preparing a pharmaceutical composition for the treatment and/or prevention of a disease or condition related to capthepsin S.

The invention also relates to pharmaceutical preparations, containing as active substance one or more compounds of formulas (I), (II) or (III), wherein X and R1 have the meanings indicated, or the pharmaceutically acceptable derivatives thereof, optionally combined with conventional excipients and/or carriers.

In order that the invention herein described may be more fully understood, the following detailed description is set forth. As used herein, the following abbreviations are used:

BOC or t-BOC is tertiary-butoxycarbonyl;

t-Bu is tertiary-butyl;

DMF is dimethylformamide;

EtOAc is ethyl acetate;

THF is tetrahydrofuran;

NMM is 4-methyl morpholine $CH_2Cl_2$ is dichloromethane;

$MgSO_4$ is magnesium sulfate;

$Na_2SO_4$ is sodium sulfate;

Ar is argon;

EDC is 1-(3-dimethylaminopropyl)-3-ethylcarbodimide hydrochloride and

HOBT is 1-hydroxybenzotriazole.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C═O). Each alkyl or alkyl analog described herein shall be understood to be optionally partially or fully halogenated.

Carbocycle refers to "aryl" being aromatic or partially saturated, or a nonaromatic cycloalkyl.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated.

The term "aryl" refers to phenyl and naphthyl.

The term "halogen" refers to a halogen radical selected from fluoro, chloro, bromo or iodo. Representative halogen groups of the invention are fluoro, chloro and bromo.

The term "heteroaryl" refers to a stable 5-8 membered (but preferably, 5 or 6 membered) monocyclic or 8-11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, The term "heterocycle" refers to a stable 4-8 membered (but preferably, 5 or 6 membered) monocyclic or 8-11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C═O).

Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

The term "amine" shall be understood to mean an $—NH_2$ group wherein each hydrogen atom may be replaced by alkyl, carbocycle, carbocyclealkyl, heteroaryl, heteroarylalkyl, heterocycle, heterocyclealkyl such that the amine nitrogen may be mono- or di-substituted by said groups.

As used herein above and throughout this application, "nitrogen" and "sulfur" include any oxidized form of nitrogen and sulfur and the quaternized form of any basic nitrogen.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

General Synthetic Methods

The invention also provides processes of making the present compounds described herein. Compounds of the invention may be prepared by methods described below, those found U.S. Pat. Nos. 6,420,364 and 6,525,052 each incorporated herein be reference in their entirety, and by methods known to those of ordinary skill in the art.

In order that this invention be more fully understood, the following examples are set forth. These examples are for the purpose of illustrating embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

SYNTHETIC EXAMPLES

Examples 1-4 illustrate the synthesis of P2 amino acid intermediates used in the synthesis of novel compounds of formula (I).

Example 1

Synthesis of 2-tert-butoxycarbonylamino-4,4,5,5-trimethyl-hexanoic acid

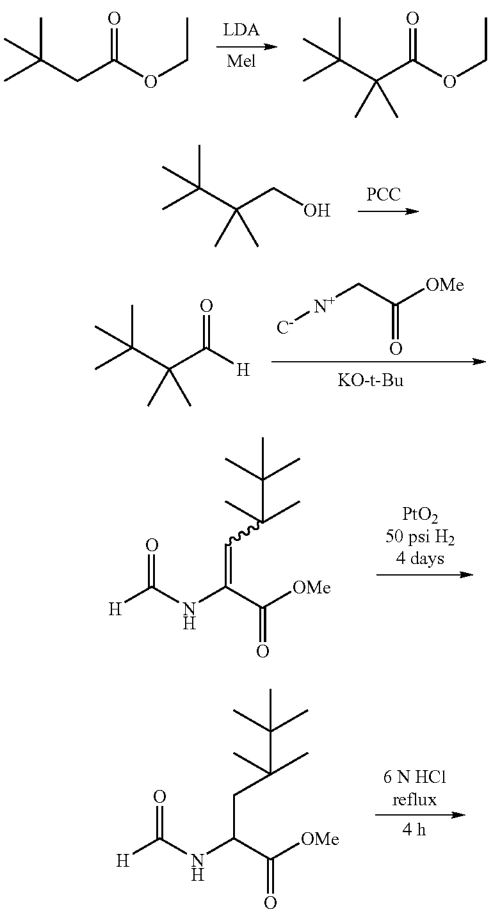

-continued

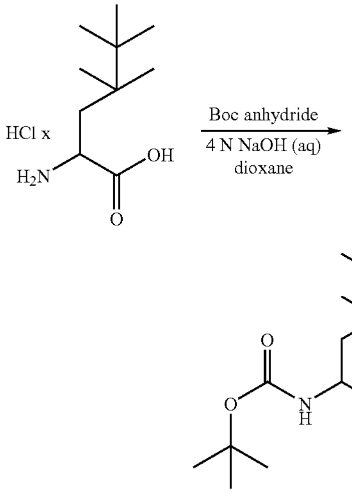

1

Lithium diisopropylamide (LDA) (1.5 M solution in cyclohexane/THF/ethylbenzene) (106 mL, 160 mmol, 1.15 equiv) was syringed into a 1000 mL round-bottom flask under a blanket of Ar. Dry THF (150 mL) was added and the mixture was cooled to −78° C. with a dry-ice/acetone bath. 3,3-Dimethyl-butanoic acid ethyl ester (20 g, 23.3 mL, 139 mmol, 1.0 equiv) was added dropwise from a syringe over a 10 min period followed by stirring at −78° C. for 1 h. Methyl iodide (9.5 mL, 152 mmol, 1.1 equiv) was added dropwise from a syringe over a 10 min period and the creamy mixture was stirred for 1 h at −78° C., resulting in a very thick mixture. The dry-ice bath was removed and replaced with an ice bath at 0° C. Another 150 mL of dry THF was added followed by another addition of LDA (106 mL, 160 mmol, 1.15 equiv). The resulting mixture was stirred for 10 min and then the flask was re-immersed in a dry-ice/acetone bath. Stirring was continued for another 50 min and then methyl iodide was added dropwise (9.5 mL, 152 mmol, 1.1 equiv) and the dry-ice/acetone bath was removed and the resulting mixture was stirred at ambient temperature for 14 h. The reaction mixture was quenched with 3 mL of concentrated HCl and 2 N HCl was added until the pH was adjusted to <1. The mixture was further diluted with 150 mL water and 500 mL $Et_2O$. The layers were separated and the organic layer was washed with 1×100 mL 2 N HCl, 1×100 mL saturated $NaHCO_3$, and 1×200 mL brine. The organic layer was dried over $Na_2SO_4$ and then concentrated in vacuo to provide 2,2,3,3-trimethylbutanoic acid ethyl ester as an orange oil mixed with ethyl benzene, 19.8 g of which (80% yield) was product by NMR. The mixture was used without further purification.

A 500 mL round-bottom flask equipped with a stir bar was flushed with Ar and charged with 50 mL dry THF and a 1 M solution of $LiAlH_4$ in $Et_2O$ (70.6 mL, 70.6 mmol, 0.625 equiv). The solution was cooled to 0° C. with an ice bath and the above ethyl ester (19.5 g, 113 mmol, 1.0 equiv) (approximately a 50% solution in ethylbenzene) was added dropwise at such a rate that the solution did not reflux (required 50 min). After addition of the ester, the reaction was stirred at 0° C. for 2 h and then at ambient temperature for 14 h. The reaction solution was re-cooled to 0° C. and carefully quenched by addition of EtOAc. 1 N NaOH was added until a granular precipitate formed (7.5 mL). The mixture was filtered on a pad of diatomaceous earth which was then washed 3×100 mL $Et_2O$. The organics were combined and dried over $Na_2SO_4$. The solution was decanted and concentrated in vacuo to yield 2,2,3,3-tetramethyl-butanol as a nearly colorless oil (12.9 g, 88% crude yield, in a mixture with ethylbenzene). The crude product was used without further purification.

A 1000 mL round-bottom-flask was equipped with a stir bar, flushed with Ar and charged with 500 mL dry $CH_2Cl_2$ and 2,2,3,3-tetramethyl-butanol (12.9 g, 99.2 mmol, 1.0 equiv). Pyridinium chlorochromate (PCC) (20.7 g, 96 mmol) was added portionwise over 5 min. The reaction mixture turned dark rapidly and was stirred at room temperature for 3 h. The reaction solvent was then decanted, washed 1 N HCl (1×250 mL), and concentrated on a rotary evaporator. The resulting pasty residue was stirred with hexanes (300 mL) for 10 min then filtered. The filtrate was dried with $Na_2SO_4$, filtered, and concentrated to provide 8.3 g (65% yield) of the desired 2,2,3,3-tetramethyl-butanal which was used without further purification.

A dry 250 mL round-bottom flask was equipped with a stir bar and flushed with Ar. Dry THF was added (40 mL) followed by addition of a 1.0 M solution of KO-t-Bu (37.5 mL, 37.5 mmol, 1.2 equiv). The solution was cooled to −78° C. in a dry-ice/acetone bath. Methyl isocyanoacetate (3.12 mL, 34.4 mmol, 1.0 equiv) was added dropwise over a 10 min period. The resulting mixture was stirred an additional 5 min followed by addition of 2,2,3,3-tetramethyl-butanal (4.0 g, 31.2 mmol, 1.0 equiv) via syringe. The cold-bath was removed and resulting mixture was stirred at room temperature for 1 h. The reaction mixture was diluted by addition of a mixture of 125 mL $Et_2O$, 20 g ice and 2 mL AcOH. After the ice melted, 50 mL of water was added and the layers were mixed and separated. The organic layer was washed with 1×50 mL sat. $NaHCO_3$ and dried over $Na_2SO_4$. The organic layer was decanted and concentrated. The crude enamide was purified by flash chromatography on silica gel using $CH_2Cl_2$ to 4% MeOH in $CH_2Cl_2$ to provide 2-formylamino-4,4,5,5-tetramethyl-hex-2-enoic acid ethyl ester as a thick oil (5.26 g, 74%); m/z calculated for $C_{12}H_{21}NO_3$ 227.3, found 228.3 $(M+H)^+$.

The above methyl ester (5.26 g, 23.2 mmol, 1.0 equiv) was dissolved in 35 mL of MeOH in a Parr bottle followed by addition of $PtO_2$ (1 g, 4.4 mmol, 0.2 equiv). The mixture was shaken on a Parr hydrogenation apparatus for 4 days at which time MS showed consumption of the starting material. The liquid was carefully decanted and the Pt was washed three times with 20 mL MeOH followed each time by decantation, being careful not to allow the Pt to dry (if allowed to dry, the Pt may ignite). The MeOH solutions containing the reduction product were combined and concentrated to a thick oil that was suspended in 25 mL of 6 N HCl and the mixture was refluxed for 4 h during which time 5 mL of concentrated HCl was added at the end of each of the first 3 h. The mixture was cooled and the water and excess HCl were removed in vacuo at a bath temperature of 70° C. After about 50% concentration, a flaky crystalline solid formed. The mixture was cooled to 0° C. and the precipitate was collected by filtration. The filtrate was again concentrated by about 50% and cooled again to 0° C. to provide a second crop of crystals. The crystals were combined and dried under high vacuum to provide 2-amino-4,4,5,5-tetramethyl-hexanoic acid hydrochloride as an off-white crystalline solid (1.40 g, 27% yield); m/z calculated for $C_{10}H_{21}NO_2$ 187.3, found 188.3 $(M+H)^+$.

The above amino acid salt (1.40 g, 6.26 mmol, 1.0 equiv) was dissolved in 100 mL of 50/50 dioxane/4 N NaOH. The solution was cooled to 0° C. and Boc anhydride (2.05 g, 9.39 mmol, 1.5 equiv) was added. The cold-bath was removed and the reaction stirred at ambient temperature for 16 h. The pH was carefully adjusted to 2 with concentrated HCl, and the product was extracted with 3×100 mL $CH_2Cl_2$. The organic layers were combined and dried over $Na_2SO_4$. The solution was decanted and concentrated using 100 mL of hexane as a chaser to provide a thick glass, which was triturated with 100 mL of hexane. After vigorous stirring for 4 h, a waxy solid resulted which was filtered and dried in air to provide the title compound (1.21 g, 67% yield); m/z calculated for $C_{15}H_{29}NO_4$ 287.4, found 286.3 $(M-H)^-$.

Example 2

Synthesis of 2-tert-butoxycarbonylamino-5,5-dimethyl-heptanoic acid

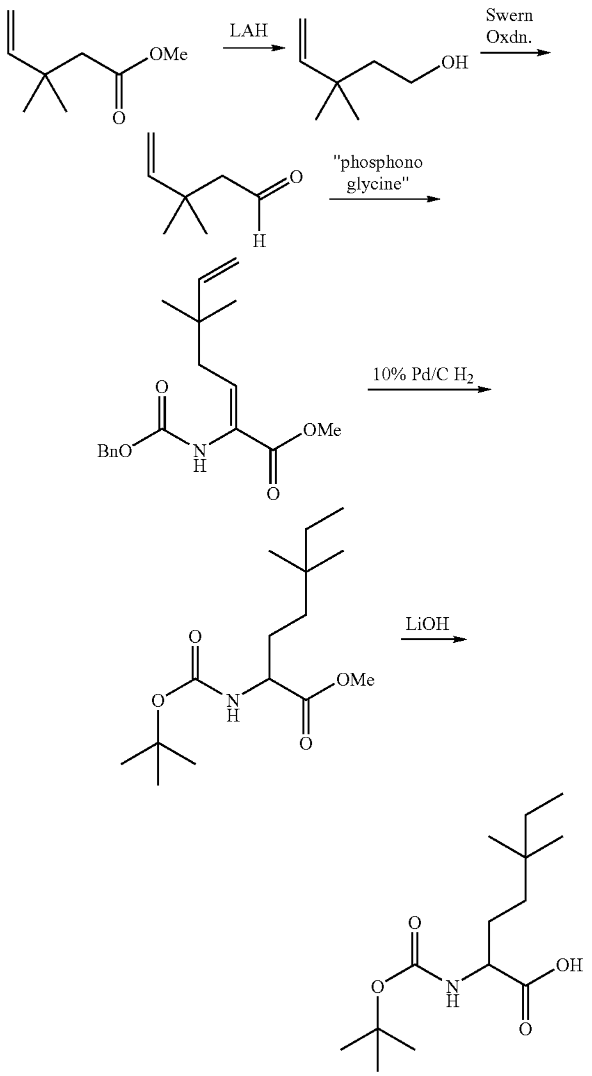

2

3,3-Dimethyl-pent-4-enoic acid methyl ester (20.0 mL, 126 mmol, 1.00 eq) was cautiously introduced via pipet into a 2 L flask containing a suspension of $LiAlH_4$ (3.63 g, 96 mmol, 0.76 eq) in 500 mL of anhydrous diethyl ether cooled by an ice water bath. The reaction mixture was allowed to warm to room temperature overnight while stirring, then quenched by slow addition of a saturated sodium potassium tartrate solution (150 mL). The mixture was diluted with ether (200 mL), and the organic layer was separated, dried ($MgSO_4$), and concentrated to provide 3,3-dimethyl-pent-4-en-1-ol as a colorless liquid (11.0 g, 76% yield). This material was used without further purification; $^1H$ NMR ($CDCl_3$, 400 MHz) δ 1.00 (s, 6H), 1.58 (t, J=7.3 Hz, 2H), 2.07 (s, 1H), 3.59 (t, J=7.3 Hz, 2H), 4.89-4.94 (m, 2H), 5.80 (dd, J=17.3, 14.1, 1H).

Anhydrous DMSO (17.1 mL, 241 mmol, 2.5 eq) was added dropwise to a solution of oxalyl chloride (10.5 mL, 120 mmol, 1.25 eq) in dry $CH_2Cl_2$ (400 mL) cooled with a dry ice/acetone bath. This solution was stirred 45 min, then 3,3-dimethyl-pent-4-en-1-ol (11.0 g, 96.3 mmol, 1.00 eq) was added via cannula as a solution in $CH_2Cl_2$ (50 mL). The resulting solution was stirred at −78° C. for 2 h. Triethylamine (54 mL, 385 mmol, 4.0 eq) was added and the cooling bath was removed. The reaction was warmed to room temperature and stirred an additional 1.5 h. The reaction mixture was then diluted with $CH_2Cl_2$ (100 mL) and washed with saturated $Na_2CO_3$ solution, followed by 1 N HCl (500 mL). The organic phase was dried ($MgSO_4$), concentrated, and the resulting residue was taken up in petroleum ether (100 mL) and filtered through a short plug of silica gel to provide the desired 3,3-dimethyl-pent-4-en-1-al (5.80 g, 54% yield) as a colorless liquid; $^1H$ NMR ($CDCl_3$, 400 MHz) δ 1.14(s, 6H), 2.33(d, J=3.1 Hz, 2H), 4.98-5.03 (m, 2H), 5.92 (dd, J=17.0, 6.0, 1H), 9.71 (t, J=3.1 Hz, 1H).

A solution of N-(benzyloxy carbonyl)-α-phosphonoglycine trimethyl ester (15.0 g, 45.3, 1.00 eq), 3,3-dimethyl-4-pent-4-en-1-al (5.64 g, 50.3 mmol, 1.11 eq), and DBU (6.8 mL, 45.5 mmol, 1.0 eq) in dry THF (150 mL) was stirred at room temperature for 16 h. The reaction mixture was diluted with ether (200 mL), washed with water (2×100 mL), then brine (100 mL). The organic layer was dried ($MgSO_4$), and concentrated. The resulting residue was chromatographed over silica gel using a gradient of ethyl acetate in hexanes as the eluant to provide the desired enamide as a yellow oil which solidified upon standing (8.60 g, 60% yield); $^1H$ NMR ($CDCl_3$, 400 MHz) δ 1.03 (s, 6H), 2.21 (d, J=7.3 Hz, 2H), 3.75 (s, 3H), 4.94-4.98 (m, 2H), 5.14 (s, 2H), 5.78 (dd, J=10.9, 10.0 Hz, 1H), 6.10-6.20 (m, 1H), 6.65 (t, J=7.3 Hz), 7.33-7.38 (m, 5H).

A suspension of 10% Pd/C catalyst (1.25 g), (Z)-2-benzyloxycarbonylamino-5,5-dimethyl-hepta-2,6-dienoic acid methyl ester (8.60 g, 27 mmol, 1.0 eq), and Boc anhydride (6.48 g, 29.7 mmol, 1.1 eq) in methanol (100 mL) was shaken on a Parr hydrogenation apparatus under 40 psi of hydrogen for 3 days. The reaction mixture was filtered through a pad of diatomaceous earth and concentrated to provide tert-butoxycarbonylamino-5,5-dimethyl-heptanoic acid methyl ester as a white solid (6.10 g, 79% yield); $^1H$ NMR ($CDCl_3$, 400 MHz) δ 0.77 (t, J=15.1 Hz, 3H), 0.80 (s, 6H), 1.1-1.3 (m, 4H), 1.42 (s, 9H), 1.55-1.65 (m, 1H), 1.7-1.8 (m, 1H), 3.74 (s, 3H), 4.20-4.35 (m, 1H), 4.95-5.05 m, 1H).

A suspension of the above methyl ester (6.10 g, 21.2 mmol, 1.00 eq) and lithium hydroxide mono hydrate (6.2 g, 148 mmol, 6.98 eq) in tetrahydrofuran (20 mL), methanol (5 mL), and water (5 mL) was stirred at room temperature for 5 h. The reaction mixture was diluted with diethyl ether (100 mL) and washed with 1N HCl (2×50 mL). The organic layer was dried ($MgSO_4$) and concentrated to provide the title compound (5.05 g, 87% yield) as a white solid; $^1H$ NMR ($CDCl_3$, 400 MHz) δ 0.74-0.82 (m, 9H), 1.10-1.28 (m, 4H), 1.45 (s, 9H), 1.52-1.63 (m, 1H), 1.75-1.90 (m, 1H), 4.20-4.30 (m, 1H), 4.94-5.02 (m, 1H).

Example 3

Synthesis of (S)-2-tert-butoxycarbonylamino-5,5-dimethyl-heptanoic acid

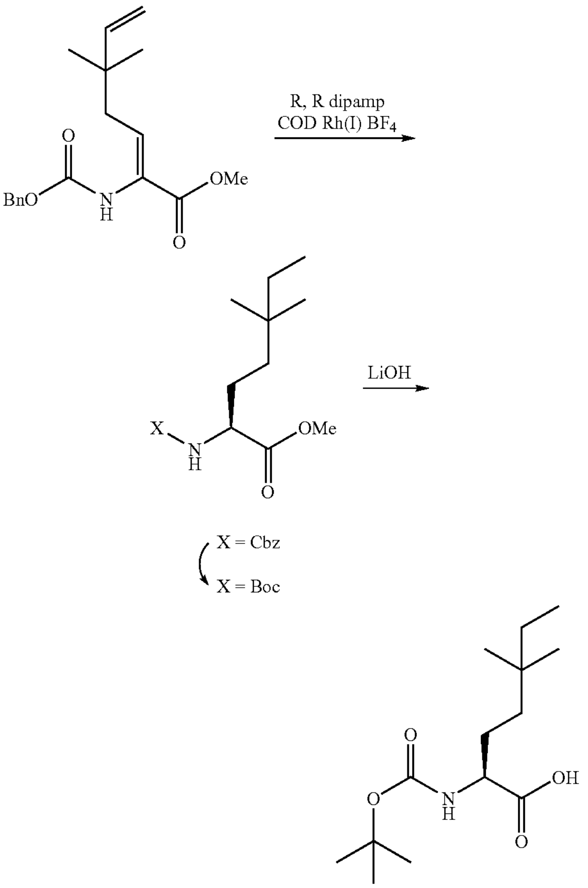

3

R,R-DIPAMP cyclooctadiene Rh(I) tetrfluoroborate (190 mg, 0.25 mmol, 0.04 eq) was added to a solution of (Z)-2-benzyloxycarbonylamino-5,5-dimethyl-hepta-2,6-dienoic acid methyl ester (2.00 g, 6.30 mmol, 1.00 eq) in dry methanol (20 mL) in a Paar hydrogenation flask. The reaction vessel was evacuated and flushed with a hydrogen atmosphere three times, then vigorously shaken under 50 psi of hydrogen overnight. The reaction mixture was concentrated in vacuo then filtered through a plug of silica gel using a gradient of ethyl acetate in hexanes as the eluant to provide (S)-2-benzyloxycarbonylamino-5,5-dimethyl-heptanoic acid methyl ester as a yellow oil (1.63 g, 81% yield); $^1H$ NMR ($CDCl_3$, 400 MHz) δ 0.74-0.90 (m, 9H), 1.10-1.30 (m, 4H), 1.58-1.70 (m, 1H), 1.75-1.90 (m, 1H), 3.75 (s, 3H), 4.30-4.40 (m, 1H), 5.14 (s, 2H), 5.24-5.33 (m, 1H), 7.30-7.37 (m, 5H); $[\alpha]^{20}_D$=+15.57 c=2.00, $CHCl_3$.

10% Pd/C catalyst (160 mg) was added to a solution of the above Cbz-protected amino acid (1.63 g, 5.07 mmol, 1.00 eq), and Boc anhydride (1.16 g, 5.32 mmol, 1.05 eq), in methanol (25 mL) in a Paar reaction vessel. The reaction mixture was shaken under 50 psi of hydrogen overnight. Filtration of the reaction mixture through a pad of diatomaceous earth and concentration of the resulting filtrate provided 1.33 g (91% yield) of the Boc protected intermediate. This material was used without further purification.

A suspension of the above Boc protected intermediate (1.33 g, 4.63 mmol, 1.00 eq) and lithium hydroxide mono hydrate (1.36 g, 32.4 mmol, 7.00 eq) in tetrahydrofuran (5 mL), methanol (2 mL), and water (2 mL) was stirred at room temperature for 5 h. The reaction mixture was diluted with diethyl ether (100 mL) and washed with 1 N HCl (2×50 mL). The organic layer was dried ($MgSO_4$) and concentrated to provide the title compound (991 mg, 78% yield) as a white solid. $^1$H NMR matches that of the racemic product (Example 2).

Example 4

Synthesis of (R)-2-tert-butoxycarbonylamino-5,5-dimethyl-heptanoic acid

4

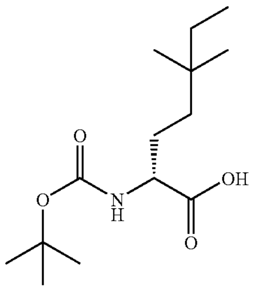

This compound was prepared via an analogous method to its enantiomer (Example 3) but substituting R,R DuPhos rhodium triflate as a catalyst for the asymmetric hydrogenation reaction. $^1$H NMR matches that of the racemic product (Example 2).

Examples 5-8 illustrate the synthesis of novel compounds of the invention described herein-above.

Example 5

Synthesis of morpholine-4-carboxylic acid [(S)-1-(4-cyano-1-methyl-piperidine-4-ylcarbamoyl)-4,4-dimethyl-hexyl]-amide

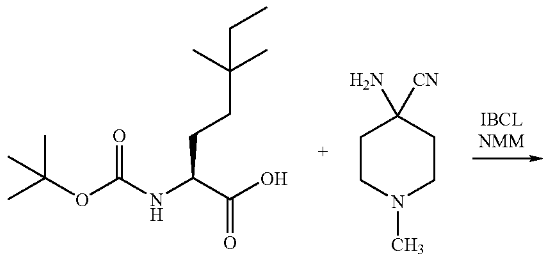

-continued

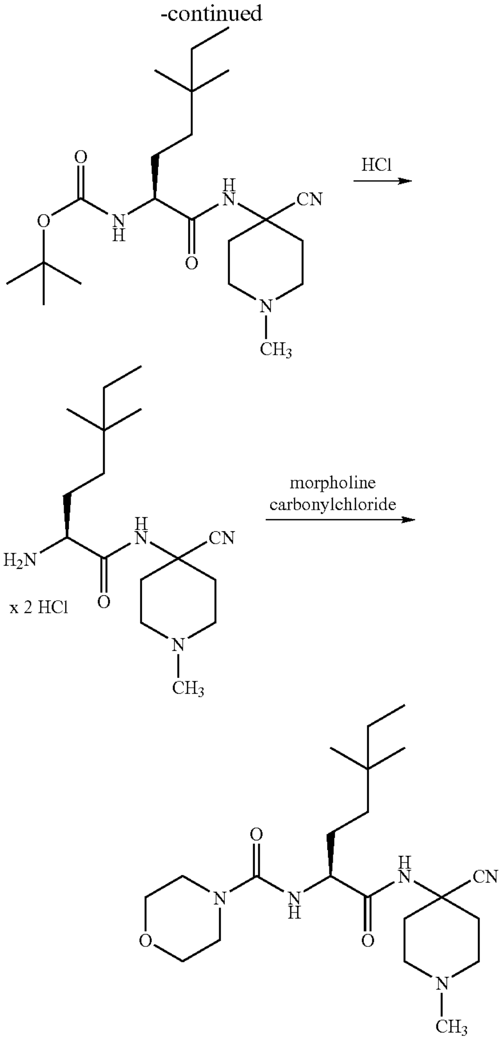

5

Isobutyl chloroformate (0.47 mL, 3.62 mmol, 1.00 eq) was added dropwise to a solution of (S)-2-tert-Butoxycarbonylamino-5,5-dimethyl-heptanoic acid (Example 3) (991 mg, 3.62 mmol, 1.00 eq), and 4-methyl morpholine (1.2 mL, 10.9 mmol, 3.00 eq) in 10.0 mL of anhydrous THF, cooled with an ice water bath. The reaction mixture was warmed to room temperature and stirred for 30 min. A solution of N-methyl piperidine amino nitrile (500 mg, 3.60, 0.99 eq) in dry THF (5.0 mL) was then added and the stirring was continued overnight at room temperature. The reaction mixture was then concentrated, taken up in ethyl acetate (50 mL), and washed with saturated $Na_2CO_3$ (2×25 mL). The organic phase was dried ($MgSO_4$) and concentrated. The resulting residue was chromatographed over silica gel using a gradient of methanol in dichloromethane as the eluant to provide 415 mg (29% yield) of the desired [(S)-1-(4-cyano-1-methyl-piperidin-4-ylcarbamoyl)-4,4-dimethyl-hexyl]-carbamic acid tert-butyl ester; m/z calculated for $C_{21}H_{38}N_4O_3$ 394.5, found 395.4 $(M+H)^+$.

The above tert-butyl ester (415 mg, 1.05 mmol, 1.00 eq) was treated with 4.0 N HCl in dioxane (10 mL) and the reaction mixture was stirred at room temperature for 2 h. The reaction mixture was concentrated, resuspended in chloroform (50 mL) and concentrated to provide the desired (S)-2-amino-5,5-dimethyl-heptanoic acid (4-cyano-1-methyl-piperidine-4-yl)-amide hydrochloride salt (307 mg, 78% yield). m/z calculated for $C_{16}H_{30}N_4O$ 294.4, found 295.1 $(M+H)^+$.

A suspension of the above hydrochloride salt (301 mg, 0.82 mmol, 1.00 eq), morpholine carbonyl chloride (0.10 mL, 0.82 mmol, 1.00 eq), and 4-methyl morpholine (0.27 mL, 2.4 mmol, 2.93 eq) in dry THF (5.0 mL) was stirred at room temperature overnight. The reaction mixture was then concentrated, taken up in ethyl acetate (50 mL), and washed with saturated $Na_2CO_3$ (2x25 mL). The organic phase was dried ($MgSO_4$) and concentrated. The resulting residue was chromatographed over silica gel using a gradient of methanol in dichloromethane as the eluant to provide 115 mg (34% yield) of the title compound as a white solid; m/z calculated for $C_{21}H_{37}N_5O_3$ 407.6, found 408.6 $(M+H)^+$. Chiral HPLC indicates >97% ee (Chirobiotic T column from Advanced Separation Technologies)

The following compounds were prepared by procedures analogous to the procedure described in the above example:

Morpholine-4-carboxylic acid [1-(4-cyano-1-propyl-piperidine-4-ylcarbamoyl)-3,3,4,4-tetramethyl-pentyl]-amide

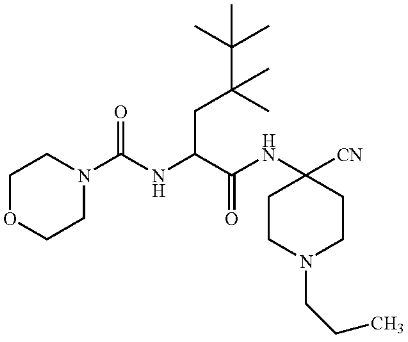

m/z calculated for $C_{24}H_{43}N_5O_3$ 449.6, found 450.6 $(M+H)^+$;

Morpholine-4-carboxylic acid [1-(4-cyano-1-propyl-piperidine-4-ylcarbamoyl)-4,4-dimethyl-pentyl]-amide

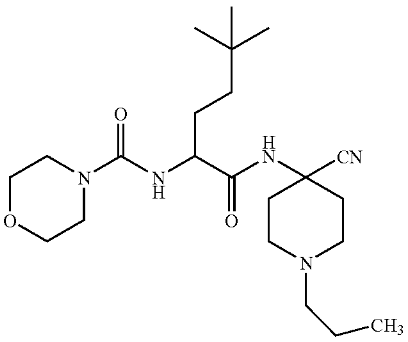

The requisite P2 amino acid intermediate, 2-tert-Butoxycarbonylamino-5,5-dimethyl-hexanoic acid, was prepared by an analogous procedure to that described for 2-tert-butoxycarbonylamino-5,5-dimethyl-heptanoic acid (Example 2) substituting the commercially available 3,3-dimethyl butan-1-al for intermediate 3,3-dimethyl-pent-4-en-1-ol; m/z calculated for $C_{22}H_{39}N_5O_3$ 421.6, found 422.9 $(M+H)^+$;

Morpholine-4-carboxylic acid [1-(4-cyano-1-propyl-piperidine-4-ylcarbamoyl)-4,4-dimethyl-hexyl]-amide

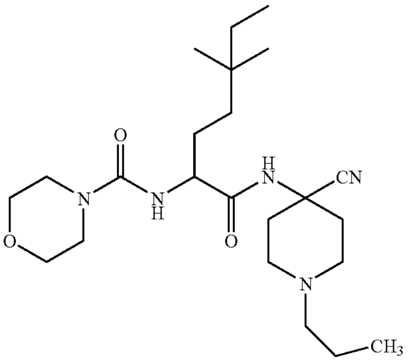

m/z calculated for $C_{23}H_{41}N_5O_3$ 435.6, found 436.5 $(M+H)^+$.

Example 6

Synthesis of morpholine-4-carboxylic acid [(S)-1-(4-cyano-1-methyl-piperidine-4-ylcarbamoyl)-4,4-dimethyl-hexyl]-amide (6)

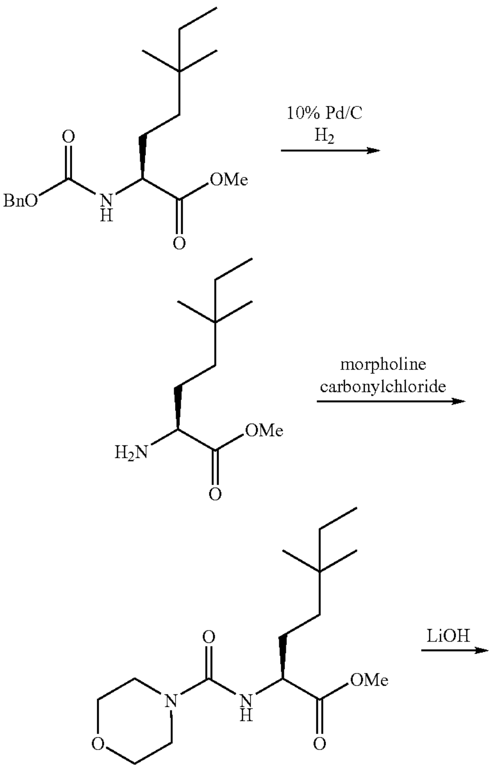

-continued

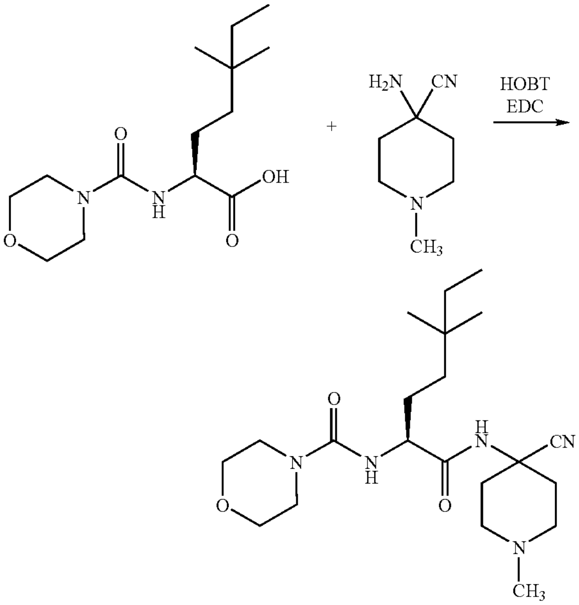

6

10% Pd/C (1.5 g) was added to a solution of Cbz protected amino acid ester (see Example 2) (27 g, 84 mmol) and ethyl acetate (135 mL). The atmosphere of the reaction vessel was evacuated and filled with 50 psi of hydrogen. The reaction mixture was shaken vigorously for 16 h then filtered through a large pad of diatomaceous earth. The filtrate was concentrated on a rotary evaporator to provide the desired amine intermediate as a light yellow oil (15.7 g, 100% yield); $^1$H NMR ($CDCl_3$, 400 MHz) δ 0.74-0.79 (m, 9H), 1.14-1.23 (m, 4H), 1.40-1.80 (m, 2H), 3.37 (t, J=3.6 Hz, 1H), 3.69 (s, 3H).

To a solution of the above amine intermediate (16.0 g, 85.4 mmol, 1.00 eq) in dry THF (300 mL) was added 4-methyl morpholine (10.4 mL, 94 mmol, 1.10 eq), followed by dropwise addition of morpholine carbonyl chloride (10.0 mL, 85.7 mmol, 1.00 eq). The reaction mixture was stirred at room temperature for 5 h, then diluted with diethyl ether (400 mL) and washed with 1N HCl (2×500 mL). The organic phase was dried ($MgSO_4$) and concentrated to provide the desired (S)-5,5-dimethyl-2-[(morpholine-4-carbonyl)-amino]-heptanoic acid methyl ester as a white solid (22.5 g, 88% yield); m/z calculated for $C_{15}H_{28}N_2O_4$ 300.4, found 301.1 $(M+H)^+$.

The above methyl ester (12.9 g, 42.9, 1.00 eq), was dissolved in methanol (60 mL) then treated with 1N LiOH (180 mL, 4.20 eq). The reaction mixture was stirred at room temperature for 2 h, then washed with diethyl ether (200 mL). The aqueous phase was then acidified to pH <1 with concentrated HCl and extracted with diethyl ether (2×200 mL). The organic phases were combined, dried ($MgSO_4$) and concentrated to provide the desired carboxylic acid (9.0 g, 73% yield); $^1$H NMR ($CDCl_3$, 400 MHz) δ 0.79 (t, J=7.5 Hz, 3H), 0.82 (s, 6H), 1.60-1.73 (m, 1H), 1.80-1.95 (m, 1H) 3.37-3.42 (m, 4H), 3.69-3.72 (m, 4H), 4.30-4.40 (m, 1H), 4.96-5.04 (m, 1H).

A mixture of the above carboxylic acid (4.5 g, 15.7 mmol, 1.08 eq), HOBT (2.93 g, 21.7 mmol, 1.5 eq), and EDC (3.06 g, 16.0 mmol, 1.10 eq) in dry dichloromethane was stirred at 0° C. for 35 min. A solution of 4-amino-1-methyl-piperidine-4-carbonitrile (2.02 g, 14.5 mmol, 1.00 eq) in dichloromethane (10 mL) was added in one portion, and the reaction mixture was allowed to warm to room temperature overnight. Solvent was removed in vacuo and the crude product was dissolved in a minimum amount of methanol and precipitated with water to provide the title compound as a white solid (2.70 g, 42% yield); m/z calculated for $C_{21}H_{37}N_5O_3$ 407.6, found 408.6 $(M+H)^+$; chiral HPLC analysis indicated >99% ee (Chirobiotic T column from Advanced Separation Technologies).

The following compound was prepared by procedures analogous to the procedure described in the above example:

Morpholine-4-carboxylic acid [(R)-1-(4-cyano-1-methyl-piperidine-4-ylcarbamoyl)-4,4-dimethyl-hexyl]-amide

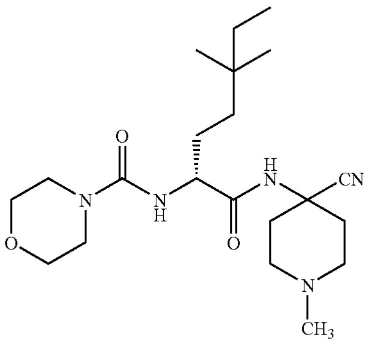

m/z calculated for $C_{21}H_{37}N_5O_3$ 407.6, found 408.6 $(M+H)^+$; chiral HPLC indicates >99% ee (Chirobiotic T column from Advanced Separation Technologies).

Example 7

Synthesis of 5,5-dimethyl-2-(2-oxo-2H-benzo[e][1,3]oxazin-4-ylamino)-heptanoic acid (4-cyano-1-propyl-piperidin-4-yl)-amide

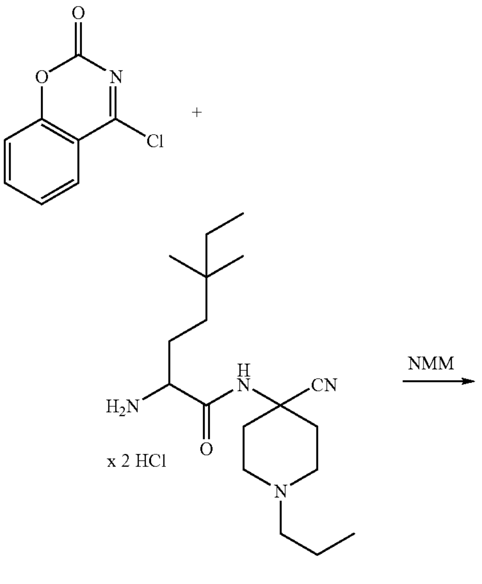

-continued

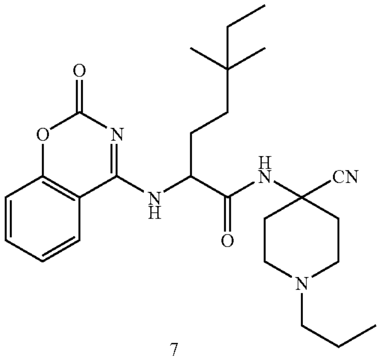

7

A suspension of 4-chloro-benzo[e][1,3]oxazin-2-one (620 mg, 3.41 mmol, 2.0 eq), 2-amino-5,5-dimethyl-heptanoic acid (4-cyano-1-propyl-piperidin-4-yl)-amide (675 mg, 1.71 mmol, 1.00 eq), and 4-methylmorpholine (NMM) (0.56 mL, 5.09 mmol, 3.00 eq) in acetonitrile (9.0 mL) was stirred at room temperature overnight. The reaction mixture was then concentrated, resuspended in ethyl acetate (50 mL) and washed with saturated $Na_2CO_3$ solution. The organic phase was dried ($MgSO_4$) and concentrated and the resulting residue was chromatographed over silica gel using a gradient of methanol in dichloromethane as the eluant to provide 124 mg (16% yield) of the title compound; m/z calculated for $C_{26}H_{37}N_5O_3$ 467.6, found 468.4 $(M+H)^+$.

The following compounds were prepared by procedures analogous to the procedure described in the above example:

5,5-Dimethyl-2-(2-oxo-2H-benzo[e][1,3]oxazin-4-ylamino)-heptanoic acid (4-cyano-1-(3-morpholin-4-yl-propyl)-piperidin-4-yl)-amide

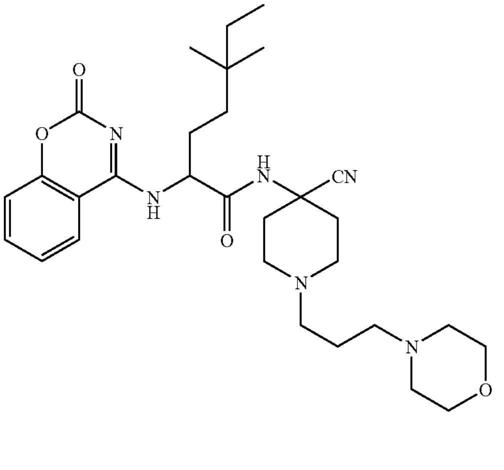

m/z calculated for $C_{30}H_{44}N_6O_4$ 552.7, found 553.9 $(M+H)^+$;

5,5-Dimethyl-2-(2-oxo-2H-benzo[e][1,3]oxazin-4-ylamino)-hexanoic acid (4-cyano-1-(2-morpholin-4-yl-ethyl)-piperidin-4-yl)-amide

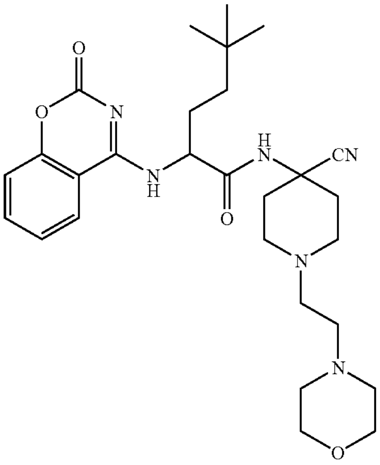

m/z calculated for $C_{28}H_{40}N_6O_4$ 524.7, found 525.5 $(M+H)^+$;

5,5-Dimethyl-2-(2-oxo-2H-benzo[e][1,3]oxazin-4-ylamino)-hexanoic acid {4-cyano-1-[2-(2-methoxy-ethoxy)-ethyl]-piperidin-4-yl}-amide

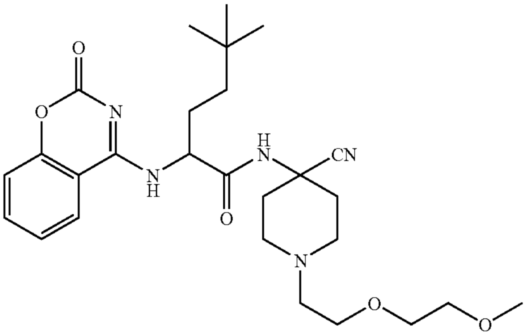

The title compound was prepared by a modification of method 3; m/z calculated for $C_{27}H_{39}N_5O_5$ 513.6, found 514.5 $(M+H)^+$;

5,5-Dimethyl-2-(2-oxo-2H-benzo[e][1,3]oxazin-4-ylamino)-hexanoic acid (4-cyano-1-methyl-piperidin-4-yl)-amide

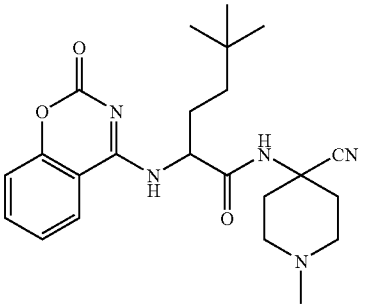

m/z calculated for $C_{23}H_{31}N_5O_3$ 425, found 426 $(M+H)^+$.

Example 8

Synthesis of 2-(7-fluoro-2-oxo-2H-benzo[e][1,3]oxazin-4-ylamino)-5,5-dimethyl-heptanoic acid (4-cyano-1-propyl-piperidin-4-yl)-amide

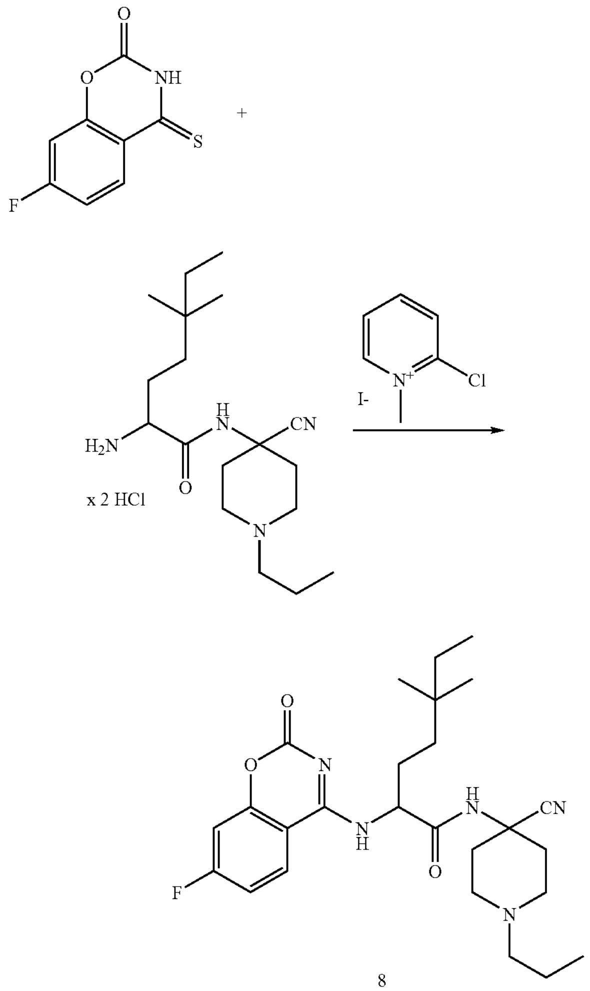

8

2-Chloro-1-methyl pyridinium iodide (365 mg, 1.43 mmol, 1.00 eq) was added to a suspension of 7-fluoro-4-thioxo-3,4-dihydro-benzo[e][1,3]oxazin-2-one (280 mg, 1.42 mmol, 1.00 eq), 2-amino-5,5-dimethyl-heptanoic acid (4-cyano-1-propyl-piperidin-4-yl)-amide (627 mg, 1.42 mmol, 1.00 eq), and N,N-diisopropyl ethylamine (1.00 mL, 5.74 mmol, 4.04 eq) in THF (10.0 mL). The reaction mixture was stirred at room temperature overnight, then concentrated, resuspended in ethyl acetate (50 mL) and washed with saturated $Na_2CO_3$ solution. The organic phase was dried ($MgSO_4$) and concentrated and the resulting residue was chromatographed over silica gel using a gradient of methanol in dichloromethane as the eluant to provide 324 mg (47% yield) of the title compound; m/z calculated for $C_{26}H_{36}F\ N_5O_3$ 485.6, found 486.5 $(M+H)^+$.

The following compounds were prepared by procedures analogous to the procedure described in the above example:

2-(7-Fluoro-2-oxo-2H-benzo[e][1,3]oxazin-4-ylamino)-5,5-dimethyl-hexanoic acid {4-cyano-1-(2-morpholin-4-yl-ethyl)-piperidin-4-yl}-amide

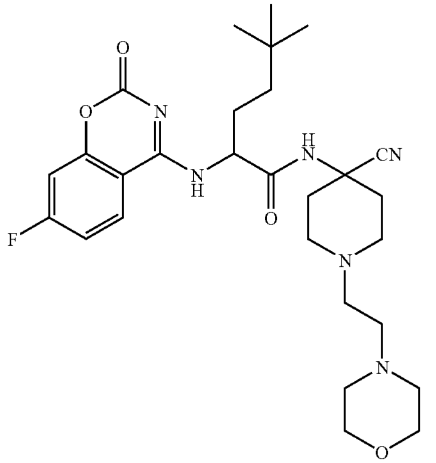

m/z calculated for $C_{28}H_{39}\ F\ N_6O_4$ 542.6, found 543.5 $(M+H)^+$;

2-(7-Fluoro-2-oxo-2H-benzo[e][1,3]oxazin-4-ylamino)-5,5-dimethyl-hexanoic acid {4-cyano-1-[2-(2-methoxy-ethoxy)-ethyl]-piperidin-4-yl}-amide

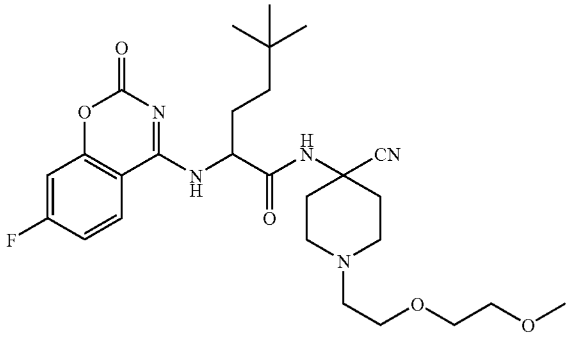

m/z calculated for $C_{27}H_{38}\ F\ N_5O_5$ 531.6, found 532.4 $(M+H)^+$.

Methods of Therapeutic Use

The compounds of the invention are useful in inhibiting the activity of cathepsin S. In doing so, these compounds are useful in blocking disease processes mediated by these cysteine proteases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis including contact and atopic dermatitis, insulin-dependent diabetes mellitus, endometriosis and asthma including allergic asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

ASSESSMENT OF BIOLOGICAL PROPERTIES

Expression and Purification of Recombinant Human Cathepsin S

Cloning of Human Cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBac1 donor plasmid (GibcoBRL, 8717 Grovemont Cr., Gaithersburg, Md. 20884) which had been cut with restriction enzyme BamH1 and blunt-ended and then cut with restriction enzyme SalI. The ligation mixture was used to transform DH5a competent cells (GibcoBRL) and plated on LB plates containing 100 ug/ml ampicillin. Colonies were grown in overnight cultures of LB media containing 50 ug/ml Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/ml kanamycin, 7 ug/ml gentamicin, 10 ug/ml tetracycline, 100 ug/ml Bluo-gal, and 40 ug/ml IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

SF9 cells were infected with recombinant baculovirus at a MOI of 5 for 48-72 hrs. Cell pellet was lysed and incubated in buffer at pH 4.5 at 37 for 2 hours to activate Cat S from pro-form to active mature form (Bromme, D & McGrath, M., *Protein Science,* 1996, 5:789-791.) Presence of Cat S was confirmed by SDS-PAGE and Western blot using rabbit anti-human proCat S.

Inhibition of Cathepsin S

Human recombinant cathepsin S expressed in Baculovirus is used at a final concentration of 10 nM in buffer. Buffer is 50 mM Na acetate, pH 6.5, 2.5 mM EDTA, 2.5 mM TCEP. Enzyme is incubated with either compound or DMSO for 10 min at 37° C. Substrate 7-amino-4-methylcoumarin, CBZ-L-valyl-L-valyl-L-arginineamide (custom synthesis by Molecular Probes) is diluted to 20 uM in water (final concentration of 5 M), added to assay and incubated for additional 10 minutes at 37° C. Compound activity is measured by diminished fluorescence compared to DMSO control when read at 360 nm excitation and 460 nm emission.

The provided examples were evaluated for inhibition of cathepsin S in the above assay. With the exception of Morpholine-4-carboxylic acid [(R)-1-(4-cyano-1-methyl-piperidine-4-ylcarbamoyl)-4,4-dimethyl-hexyl]-amide, all had $IC_{50}$ values of 100 nM or below.

Inhibition of Cathepsin L

This protocol is identical to that described above for measuring Cathepsin S inhibition with the exception that human Cathepsin L (Athens Research, Georgia) is substituted for Cathepsin S.

The provided examples were evaluated for inhibition of cathepsin L in the above assay. All had $IC_{50}$ values of about or greater than 1000 nM.

With the exception of Morpholine-4-carboxylic acid [(R)-1-(4-cyano-1-methyl-piperidine-4-ylcarbamoyl)-4,4-dimethyl-hexyl]-amide, the examples above demonstrate between a 50 and 5000 fold selectivity for cathepsin S over cathepsin L based on these molecular assays (calculated as cathepsin L $IC_{50}$/cathepsin S $IC_{50}$).

What is claimed is:

1. A compound of the formula (I) or (II):

(I)

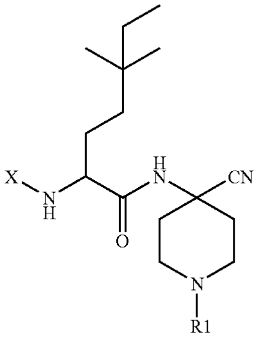

(II)

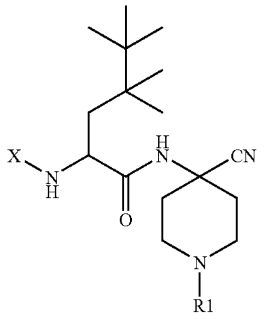

wherein X is

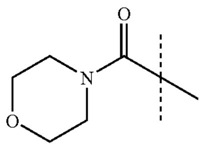

and;

R1 is chosen from hydrogen or alkyl branched or straight chain alkyl, each carbon atom in the chain is optionally replaced with one to three heteroatoms chosen from O, S, and N—R2 wherein R2 is hydrogen or alkyl;

and wherein R1 is optionally further substituted by one or more alkoxy, amine, halogen, carbocycle, heteroaryl or heterocycle;

or the pharmaceutically acceptable salts thereof.

2. The compound according to claim 1 wherein:

in the formula (I)

(I)

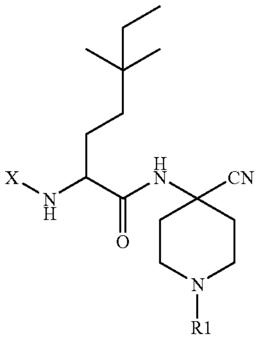

R1 is chosen from hydrogen or C1-10 alkyl branched or straight chain C1-10 alkyl, each carbon atom in the chain is optionally replaced with one to three heteroatoms chosen from O, S, and N—R2 wherein R2 is hydrogen or C1-5 alkyl;

and wherein R1 is optionally further substituted by one or more C1-5 alkoxy, amine, heterocycle or halogen.

3. The compound according to claims 1 or 2 wherein of R1 is C1-5 alkyl.

4. The compound according to any of claims 1, 2 or 3 wherein of R1 is C1-3 alkyl.

5. The compound according to claims 1 or 2 wherein R1 is chosen from:

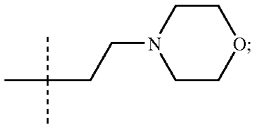

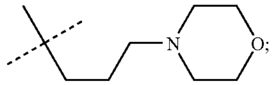

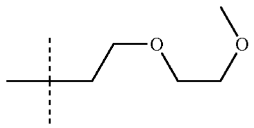 and 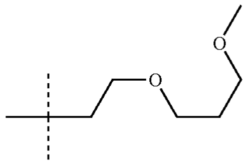 .

6. The compound according to any of claims 1-5 wherein the compound of the formula (I) is the (S) enantiomer which possesses a natural amino acid configuration at the indicated chiral carbon below (I)

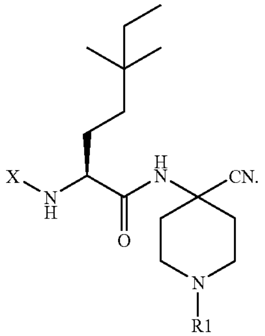

7. A compound chosen from

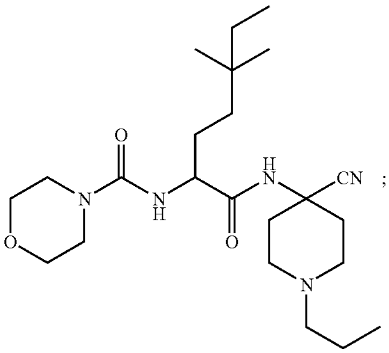

;

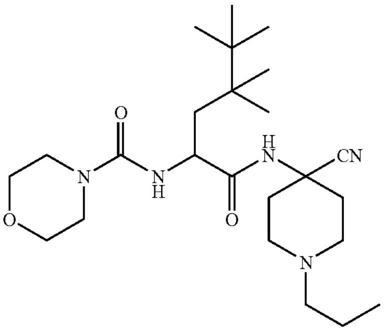

and

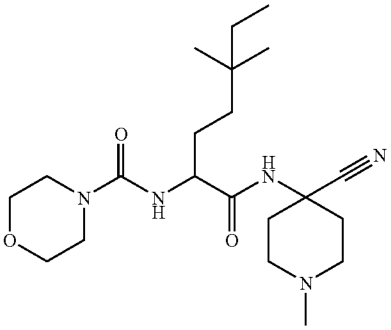

or the pharmaceutically acceptable salts thereof.

8. A compound or the pharmaceutically acceptable salts thereof wherein the compound is:

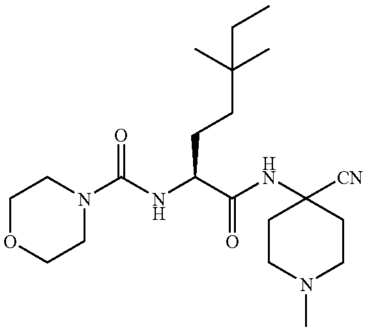

wherein the indicated chiral carbon is the (S) enantiomer which possesses a natural amino acid configuration.

9. A compound wherein the compound is:

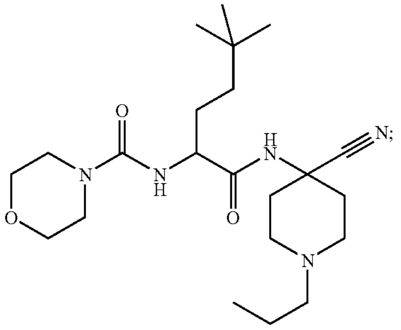

or the pharmaceutically acceptable salts thereof.

10. A method of treating a disease or condition chosen from:

rheumatoid arthritis, multiple sclerosis, and atherosclerosis; comprising administering to a patient a pharmaceutically effective amount of a compound according to claim 1.

* * * * *